(12) United States Patent
Hagerman et al.

(10) Patent No.: US 10,010,809 B2
(45) Date of Patent: Jul. 3, 2018

(54) THIN-FILM TREATMENT OF HIGH-VALUE GLYCOL AND AMINE SOLVENTS TO REMOVE CONTAMINANTS

(71) Applicant: MPR Services, Inc., Alvin, CA (US)

(72) Inventors: David Thomas Hagerman, Houston, TX (US); Irwin John Seward, Jr., Freeport, TX (US)

(73) Assignee: MPR Services, Inc., Phoenix, AZ (US)

( * ) Notice: Subject to any disclaimer, the term of this patent is extended or adjusted under 35 U.S.C. 154(b) by 179 days.

(21) Appl. No.: 14/768,947

(22) PCT Filed: Feb. 19, 2014

(86) PCT No.: PCT/US2014/017223
§ 371 (c)(1),
(2) Date: Aug. 19, 2015

(87) PCT Pub. No.: WO2014/130588
PCT Pub. Date: Aug. 28, 2014

(65) Prior Publication Data
US 2016/0001197 A1    Jan. 7, 2016

Related U.S. Application Data

(60) Provisional application No. 61/850,544, filed on Feb. 19, 2013.

(51) Int. Cl.
| | | |
|---|---|---|
| *B01D 1/22* | (2006.01) |
| *B01D 3/14* | (2006.01) |
| *B01D 3/10* | (2006.01) |
| *C07C 29/76* | (2006.01) |
| *C07C 213/10* | (2006.01) |
| *B01D 3/34* | (2006.01) |
| *B01D 53/14* | (2006.01) |

(52) U.S. Cl.
CPC ............ *B01D 3/148* (2013.01); *B01D 1/22* (2013.01); *B01D 1/225* (2013.01); *B01D 3/10* (2013.01); *B01D 3/346* (2013.01); *B01D 53/1425* (2013.01); *C07C 29/76* (2013.01); *C07C 213/10* (2013.01); *B01D 2252/2023* (2013.01); *B01D 2252/2025* (2013.01); *B01D 2252/2026* (2013.01); *B01D 2252/2028* (2013.01); *B01D 2252/20478* (2013.01)

(58) Field of Classification Search
CPC .... B01D 1/225; B01D 3/346; B01D 53/1425; B01D 1/22; B01D 3/10; B01D 2252/20478; B01D 2252/2025; B01D 2252/2026; B01D 2252/2028; B01D 2252/2023; C07C 213/10
See application file for complete search history.

(56) References Cited

U.S. PATENT DOCUMENTS

| 4,267,077 | A | * | 5/1981 | Niimi ........................ D06L 1/04 510/287 |
| 5,102,503 | A | | 4/1992 | Silinski et al. |
| 6,152,994 | A | * | 11/2000 | Van Grinsven ....... C07C 213/10 203/42 |
| 6,265,625 | B1 | | 7/2001 | Vansant et al. |
| 6,316,399 | B1 | * | 11/2001 | Melikyan ............... C11D 1/831 510/372 |
| 7,316,781 | B2 | * | 1/2008 | Radomyselski .......... D06L 1/10 159/47.1 |
| 2011/0100561 | A1 | | 5/2011 | Alasti et al. |

FOREIGN PATENT DOCUMENTS

| WO | 00/76624 | 12/2000 |
| WO | 2011/053983 | 5/2011 |

OTHER PUBLICATIONS

Solid. (n.d.) in Oxford English Dictionary. Oxford University Press (https://en.oxforddictionaries.com/definition/solid).*
Rosen, M. J. et al. (2012). Surfactants and Interfacial Phenomena, 4th Edition. NJ: Wiley.*
Shah, 1988, Heat transfer equipment design: Advanced study institute book. CRC Press, New York.*
Extended search report dated Nov. 21, 2016, of European Patent Office in corresponding EPO Patent App. No. 14753535.5 (12 pages).
International Search Report dated Aug. 18, 2014 in International Application No. PCT/US2014/017223.
Written Opinion of the International Searching Authority dated Aug. 18, 2014 in International Application No. PCT/US2014/017223.
International Preliminary Report on Patentability dated Aug. 25, 2015 in International Application No. PCT/US2014/017223.

* cited by examiner

*Primary Examiner* — In Suk C Bullock
*Assistant Examiner* — Youngsul Jeong
(74) *Attorney, Agent, or Firm* — Fennemore Craig, P.C.

(57) ABSTRACT

A method for cleaning a contaminated solvent used to treat a gas stream, for example a contaminated glycol or a contaminated amine stream, by vacuum evaporation using a mechanically-maintained horizontally-orientated thin film evaporator, where the contaminant material is recovered from the thin film in solvent-free form, as either a heavy organic material or as free flowing salts.

22 Claims, No Drawings

THIN-FILM TREATMENT OF HIGH-VALUE GLYCOL AND AMINE SOLVENTS TO REMOVE CONTAMINANTS

This application claims priority as a continuation in part to U.S. provisional application No. 61/850,544 titled THIN-FILM TREATMENT OF GLYCOL TO REMOVE WATER AND SALTS filed on Feb. 19, 2013.

FIELD OF THE INVENTION

The invention relates to a method of removal of salts and contaminants from a glycol stream, an amine stream, or a mixed stream of one or more selected solvents by utilizing a horizontally-orientated mechanically maintained thin film evaporator operated at modest temperature and absolute low pressure, thereby forming a dry film of salt contaminants and/or solid contaminants within the thin film evaporator, wherein said contaminants are substantially solvent free and are in the form of flowable solids or a tar-like substance, and recovering the substantially contaminant-free glycol and/or amine.

BACKGROUND OF THE INVENTION

Certain solvents are used in industry to scrub gases. These solvents must be routinely cleaned and re-used. There are two general classes of solvents—chemical and physical. Chemical solvents react with impurities, while physical solvents remove impurities due to the solubility of the impurities in the solvents. Generally, pot distillation, ion exchange, and/or chemical treatments have been used to treat (reclaim) solvents after the solvent effectiveness is reduced. Solvents particularly needing reclamation include ethylene and/or propylene glycols, certain amines including alkanolamines, propropylene carbonate, NMP, as well as proprietary solvents such as di-alkyl ethylene and/or propylene glycols (of which Selexol, a mixture of the dimethyl ethers of polyethyleneglycol, is included). Certain solvents, such as Selexol, Sulfinol, and the like, are purely physical solvents, while certain chemical solvents such as ethanolamines react with impurities in the gases.

Similarly, there are three general classes of impurities which build up in the solvents. These include salts, solids, and heavy hydrocarbons.

After use, it may contain, in addition to water and glycols, specific contaminants according to origin and field of use. Glycol is often used to remove water from gas streams, and control hydrates in multiphase transmission pipelines. Further, large amounts of liquids containing glycol, especially ethylene glycol, are obtained in the manufacture of polyesters, especially polyester fibers; these liquids also contain, in addition to water, other impurities stemming from the process. Glycol streams, which include (poly)ethylene glycol, (poly)propylene glycol, (poly)ethylene/propylene glycols, and the like, typically contain water, solids, dissolved organic contaminants, and dissolved inorganic contaminants which are usually ionic. The glycol streams must be regenerated.

Large amounts of amine are used industrially. After use, it may contain, in addition to water and amine, specific contaminants according to origin and field of use. Amines, particularly alkanolamines, are used to remove acid gases from gas streams. Amine streams, which include alkanolamines such as monoethanolamine, diethanolamine, methyldiethanolamine, diisopropylamine, and aminoethoxyethanol, typically contain water, solids, dissolved organic contaminants, and dissolved inorganic contaminants which are usually ionic. The amine streams must be regenerated. Ion exchange or chemical precipitation are known methods of removing ionic components including salts, but these do not remove non-ionic organics. The constituents removed by ion exchange are typically characterized as amino acids and inorganic and organic salts which are formed in a petrochemical processes or are introduced in the gas treatment train process. When isolated as pure substances at room temperatures, these amino acids and salts are solids and are water soluble. These constituents are effectively removed by ion exchange processes at the expense of large volumes of easily treated waste brine water. The removal may be less than optimum and the introduction of water during treatment is often an inefficiency. Because these constituents are solids with high melting temperatures, vacuum distillation can also remove them by a very inefficient process of boiling of liquids. The distillation process is inefficient due to fouling of heat transfer surfaces, as well as additional solvent degradation due to the long exposure to heat and reactions between the solvent and impurities. Amine solvent may undergo degradation, whereby undesired degradation products are formed in the liquid phase. These degradation products, known as heat stable salts or heat stable amine salts, may accumulate in the circulating absorbent stream. For amine streams, the constituents not removed by ion exchange are chemical products of dehydration or reaction with carbon dioxide. This class of chemical substances can contain diamines, triamines, urea, esters and a myriad of other named and unknown chemical species. These species, when isolated at room temperature, can be solids; semi-solids; or viscous liquids and do not tend to exhibit significant ionic behavior when dissolved in water.

For glycol streams, particularly monoethylene glycol commonly employed to dehydrate natural gas as an initial step after gathering and prior to further processing, the process causes the glycol to absorb water and in the process become contaminated with naturally occurring and corrosion-generated salts. The glycol has to be dehydrated prior to being recycled in the natural gas production process. The glycol dehydration process is a type of distillation where the absorbed water is removed by heating and refined in a distillation column. The heat source in this process is a reboiler that applies the heat to a hot glycol at the bottom of this column contaminated with the salts and corrosion products resulting in a fouling condition. Use of straight-forward distillation to remove water is known. However, distillation can result in hot temperatures for long durations, and various organics and inorganics in the glycol stream tend to react with one another and with the glycol to form undesirable byproducts. Cleaning a glycol stream with a Kettle Reboiler Reclaimer results in high solvent loss due to degradation. Frequent cleanout is required for reclaimer to work. This process is ineffective or in-operative in removing certain ionic components, particularly chlorides. The contaminant accumulates in reclaimer and in the circulation of the system until removed by a scheduled cleanout. Alternatively, kettle reboiling can be combined with a second ion exchange process to remove chlorides from systems with these reclaimers.

Vertically-oriented thin film evaporators have been used to evaporate certain selected solvents, where the thin film evaporators have plates orientated in a vertical direction, where a thin film of solvents flows over plates to speed up the process of evaporation of the solvent. The thin film may be mechanically agitated. Residual solvent carrying the impurities flows to the bottom of the plates where this material is disposed of or additionally reclaimed. Deficiencies include high solvent losses due to liquid (solvent) hold up in the vessel, bearing problems, thinning of the film, and slurry buildup caused by excess solvent in the bottoms is difficult to control. The contaminant removed is typically high in solvent content, typically having at least 15 wt % or more solvent.

Evaporation is a single-step in a distillation process, such as reboiling liquids in the bottom of a distillation column. Evaporation offers the possibility of removing all but a small fraction of both classes of undesirable constituents from contaminated amine solutions and salts from glycols in a single processing step. Evaporation in conventional evaporators has met with varying degrees of success due to the increased fouling of the heat transfer surfaces by the very contaminants the process was attempting to remove.

It is known to remove undesirable contaminants by vacuum distillation. In this process, water is typically removed first, and then the glycol itself is distilled off, leaving heavy organics and solids. This distillation process is not only effective on undesirable constituents that are not ionic in nature and cannot be removed by ion exchange, but also can remove the class of undesirable constituents that can be removed by ion exchange. The major drawbacks to the distillation process are poor heat transfer, degradation of heat transfer capability, the process necessity to waste significant quantities of the amines and glycols and for amines, their further degradation in the reclaimer. Further, distillation is typically a batch process, which is more labor intensive than steady state processes.

Forced Circulation Evaporator is also a process to clean solvents. Again, deficiencies include high solvent loss due to liquid hold up in the vessel and slurry build up in reclamation circulation. Further, the bottoms of such evaporator systems have high solvent content from 30 to 70 wt % depending on when the system is purged, resulting in a significant amount of solvent lost as the contaminant level is increased (from 3 to 20 wt %). This process is not considered commercially feasible.

SUMMARY OF THE INVENTION

The invention in a first embodiment provides a steady-state method of treating a contaminated solvent stream, the process comprising: a) providing a first stream of contaminated solvent comprising an amine, a glycol, or mixture thereof, and one or more contaminants comprising salts, organics, solids, or mixtures thereof typically salts and/or organic material; b) forming and mechanically maintaining a thin film of contaminated solvent disposed on a substrate surface at sub-atmospheric pressure, said thin film having a thickness, wherein the thin film is repeatedly wiped to maintain a film thickness and to move the film along the substrate surface; c) recovering a tops vapor phase comprising the solvent, wherein the concentration of contaminants in the recovered solvent is substantially reduced from the concentration of contaminants in the first stream, and d) recovering a bottoms phase from the substrate surface, wherein the bottoms phase recovered from the substrate surface comprises contaminants and is a flowable solid material or a tar-like material, said bottom phase comprising less than 20% by weight solvent. The first stream is a feed stream. Advantageously the bottoms phase recovered from the substrate surface comprises less than 10% by weight solvent, and more preferably the bottoms phase recovered from the substrate surface comprises less than 5% by weight solvent. Most preferably the bottoms phase recovered from the substrate surface comprises less than 1% by weight solvent, which can in many locations allow the waste to be treated as non-hazardous material.

In another embodiment of the invention, the first stream of contaminated solvent comprises a glycol solvent and contaminant salts, and the bottoms phase recovered from the substrate surface is a flowable powder. Advantageously the bottoms phase recovered from the substrate surface is a flowable powder containing substantially no glycol. In preferred aspects of this invention, the tops vapor phase comprising the solvent is condensed to recover the glycol, wherein the glycol loss is 5% by weight or less, preferably 1% by weight or less, based upon solvent mass balance. Advantageously the recovered contaminants have 10% by weight or less of solvent, more preferably 5% by weight or less of solvent, for example 1% by weight or less of solvent. Alternatively, the tops vapor phase comprising the solvent is condensed to recover the glycol, wherein the glycol recovered is 95%, more typically 99%, by weight or more of the glycol in the first stream, based upon solvent mass balance, and wherein the recovered contaminants have 10%, more typically 5%, by weight or less of solvent. By glycol we mean a solvent which comprises or consists essentially of a glycol, for example wherein the glycol is selected from ethylene glycol, propylene glycol, diethylene glycol, triethylene glycol, tetraethylene glycol, polyethylene glycol, polypropylene glycol, polyethylene/propylene glycols, methyl ethers of polyethylene glycols, methyl ethers of propylene glycols, and mixtures thereof.

In another embodiment of the invention the first stream of contaminated solvent comprises an amine solvent and contaminants and also comprises contaminant organics and/or contaminant thermally stable salts. The most important amine solvents are alkanolamines, and specifically include alkanolamines selected from the group consisting of monoethanolamine, diethanolamine, triethanolamine, 2-(2-Aminoethoxy)ethanol, methyl diethanolamine, di-isoprpanolamine, Flexsorb™ proprietary alkanolamine, Cansolv™ proprietary alkanolamine, and mixtures thereof. In this embodiment, advantageously the bottoms phase recovered from the substrate surface is a tar-like material which contains 20% by weight or less of solvent, for example 10% by weight or less of the solvent. The solvent may comprise or consist essentially of an amine, by which we define amines to include functional amines such as alkanolamines, and advantageously the tar-like material recovered from the substrate surface comprises 5% by weight or less of the amine and/or 5% by weight or less of the solvent. In a preferred embodiment of the invention, the tops vapor phase comprising the solvent is condensed to recover the solvent, and the solvent loss is 5% or less, preferably 1% or less, by weight based upon solvent mass balance, and wherein the recovered contaminant material comprises 10% by weight or less of solvent. Alternatively, the tops vapor phase comprising the alkanolamine is condensed to recover the alkanolamine, wherein the alkanolamine recovered is 95%, more typically 99%, by weight or more of the alkanolamine in the first stream, based upon solvent mass balance, and wherein the recovered contaminants have 10%, more typically 5%, by weight or less of alkanolamine.

In another embodiment of the invention, the tops vapor phase comprising the solvent is condensed to recover the glycol, wherein the glycol recovered is 99% by weight or more of the glycol in the first stream based upon solvent mass balance, and wherein the recovered contaminants have 5% by weight or less of solvent.

Such solvent recovery and recovery of the contaminant material from the thin film is not readily possible with vertical thin films, even if mechanically maintained, because downward flow caused by gravity results in greater levels of solvent in the recovered bottoms. Advantageously for the various aspects of this invention the substrate surface is a substantially horizontal plane or is a cylindrical wall or portion thereof wherein the axis of the cylinder is substantially horizontally orientated. Advantageously the thin film has a thickness between about 1 and about 5 mm, and the thin film is mechanically maintained by repeatedly being contacted by wipers which provide additional contaminated solvent to maintain a film thickness and which move the film along the substrate surface. Generally the pressure is subatmospheric, and may be 10 kPa or less, for example 5 kPa or less.

An important aspect of the invention is the removal and recovery of the contaminant phase as a substantially solvent-free material, whether this material has a tar-like consistency or has the consistency of a free-flowing powder. In the case where the recovered materials are salts, the material might be handled as a non-hazardous material, which greatly simplifies waste handling. Contaminant salts in glycol can be recovered as free-flowing powder, with over 99% by weight of solvent entering the process being recoverable from the vapor phase. Contaminant material in amines can be recovered as a liquid or a tar, with over 99% by weight of solvent entering the process being recoverable from the vapor phase. The process uses a mechanically agitated thin film evaporator, which is advantageously in the form of a horizontal cylinder configuration. The process is steady state and can accept high flow rates and short residence time in the evaporator, i.e, residence time in 30 to 90 seconds range, resulting in minimal additional thermal degradation of solvent.

Another embodiment includes a process of treating a contaminated solvent stream, for example a contaminated glycol stream or a contaminated amine stream, by a) introducing contaminated solvent to a mechanically-formed moving thin film on a horizontally orientated heated substrate under conditions of elevated temperature and subatmospheric pressure, wherein the contaminated solvent forms a mechanically maintained thin film on the horizontally-orientated substrate, or alternatively on a cylindrical wall or portion thereof wherein the axis of the cylinder is horizontally orientated, b) mechanically moving and agitating the thin film for a time sufficient to remove substantially all the solvent, and the recovered contaminants are recovered in substantially solvent-free form. The thin film can be mechanically maintained by continuous or intermittent wipers passing over the film, maintaining for example a film thickness of between 1 mm and 5 mm. Solvent, or alternatively volatile contaminants, are evaporated under a sufficiently elevated temperature and a sufficiently low pressure, where the pressure is less than atmospheric pressure (is a vacuum). Countercurrent flow is used, wherein the volatiles (tops phase) moves in a direction opposite the direction the wipers are moving the thin film material. Alternatively or additionally, a sparge gas, typically an inert gas, can be used to facilitate removal of the vapor phase from the evaporator. As used herein the term "inert gas" refers to a condensable gas that will not react with the solvent or contaminants under the process conditions described herein. Steam is a preferred inert gas used in the processes as a sparge gas.

The thin film is advantageously maintained at an absolute pressure of between about 0.1 and 200 kPa, typically between 1 and 50 kPa, usually between 1 and 20 kPa, and for many solvents is advantageously maintained at between 1 and 10 kPa, for example between 2 and 5 kPa.

Advantageously the substrate or surface on which the thin film resides can be a horizontally oriented cylinder, where the thin film is maintained on the inside and/or outside of the cylinder. Typically the thin film is maintained on the inside cylindrical wall, so that centrifugal force pushes film material against the wall. This evaporator configuration is better able to obtain solid contaminants as dry powder or as concentrated solvent-free form that greatly simplifies waste handling.

The processes are advantageous to remove contaminants and degradation products from a variety of solvents including especially amines and glycols, to remove the majority constituents of interest.

Generally, if the recovered contaminant phase is organic, the material will have the consistency of a syrup or tar. The exact consistency will of course depend on the composition of the contaminants. By tar-like we generally mean a viscosity at room temperature of greater than 10000 centipoise. The consistency of a recovered organic phase is secondary to the point that the recovered contaminant material is substantially solvent-free, having at a minimum 20% or less by weight solvent, more preferably 10% or less by weight solvent, for example 5% or less by weight of solvent, and in certain cases 1% of less by weight of solvents.

Advantageously, the contaminated solvent stream is treated in a horizontally oriented mechanically maintained thin film treatment apparatus operating at steady state, and the residual recovered contaminants contain less than 10%, for example 5%, of the solvent originally introduced to the reclamation process, and advantageously contain less than 1% of the solvent originally introduced to the reclamation process. Multiple passes may be required to remove both volatile and non-volatile contaminants, if it is desired to remove certain contaminants that are more volatile than the solvents, as well as to remove certain contaminants that are less volatile than the solvent. Traditional vertical thin films are typically limited to 20% or more of the solvent originally introduced to the reclamation process being in the resulting contaminant stream. Waste composition of salt or other contaminants in the described inventions will typically have from 20 wt % or less solvent.

A horizontal-axis wiped film thermal evaporator can remove contaminants from certain solvents. By horizontal we mean a substantial portion of the flat substrate supporting the thin film, or more typically a substantial portion of the cylinder or cone whose wall supports the thin film, is substantially horizontal. The orientation of a cone or cylinder is the orientation of the axis thereof. While a preferred orientation is horizontal, in less preferred configurations the substrate can be somewhat off horizontal, for example forming an angle of 30 degrees or less from horizontal, preferably less than 10 degrees from horizontal.

As is known in the art, the thin film is mechanically maintained by periodic wipers, said wipers re-establishing the thin film and also preventing localized dry spots leading to fouling and "burn-on;" which are typical problems with normal distillation processes. Said wipers move an excess of material which forms the thin film before the wiper, so that the thickness of the film can be maintained. An important aspect of the horizontally oriented mechanically maintained thin film evaporator is that, unlike vertically oriented evaporators, there is no bottom "steady" bushing that would otherwise need continuous lubrication and flushing. Generally, the recovered contaminant streams, be they heavy hydrocarbons, hetero-molecules, or salts, are sticky, abrasive, and corrosive. Maintaining a bushing in contact with such vertically oriented substrate material is an operational problem where potential solutions, e.g., flushing a bottom bearing with solvent or with lubricant, results in lower recovery efficiency, increasing the contaminant load, or both.

The horizontally-orientated wiped thin film evaporator has moving components, often called wipers, which when driven over the thin film facilitate evaporation at the surface wall due to mechanical shear and heat at the wall. By "wall," "substrate," or "evaporating substrate" we mean the surface on which the thin film resides during the evaporation. Wipers or blades are maintained a fixed small distance from the evaporating substrate, and these wipers or blades are operative to redistribute and/or move the evaporating film of solvent and contaminants along the face of the evaporating substrate. By periodic we mean the wipers move over the surface of the thin film at least once every 10 seconds, and typically a wiper will move over a given surface of the thin film multiple times per second, and generally at significant velocity, for example 20 to 75 ft/sec. The horizontal forced circulation imparted by wipers in preferred embodiments does not have significant liquid holdup, but contains sufficient contaminated solvent to allow wetting the covered surface area, said liquid before the wiper being pushed forward by sheer force of the wiper.

The vertical wiped film evaporator used in the art may more typically have liquid hold up so that the solvent can be evaporated by mechanical shear at the wall, conductive heat from the wall and heat of the bulk solution in the bottom. The forced circulation evaporator has similar heating requirements of from the bulk solution heating the inlet feed.

In another embodiment, the invention includes a process of treating a contaminated glycol stream, by mechanically forming a moving thin film on a heated substrate under conditions of elevated temperature and sub-atmospheric pressure, wherein the residence time on the thin film evaporator is sufficient to remove substantially all the glycol stream, respectively, and the recovered ionic material is stored at reduced pressure, such that the recovered ionic contaminants are recovered in dry powder form. The thin film is mechanically maintained by continuous wipers to a thickness of between 1 and about 5 mm, for example about 2 to 3 mm, thickness. The unit advantageously dries the thin film such that the residual contaminants, which are primarily salts, are recovered as free flowing powder. This obtaining of the contaminant salts, and the like, as powder greatly simplifies waste handling.

In another embodiment the process advantageously removes contaminants and degradation products from amines and glycols used by refinery, natural gas and petrochemical processes, wherein a single treatment may remove the majority of contaminants of interest. Solvent waste is lower than other vacuum distillation reclamation technologies, and the process saves the disposal and minimizes environmental impact. The invention reduces waste and increases life span of the fluid and potentially reduces corrosion of system metallurgy.

The horizontal wiped film evaporator is advantageously used in place of commercially available kettle horizontal reboilers or other vacuum distillation techniques including vertical wiped film evaporators.

The solvent loss is lower than any other known vacuum distillation, and is typically 5% by weight or less, more typically 1% by weight or less, of solvent loss based upon solvent mass balance (total solvent recovered versus total solvent in contaminated feed) for rapid commercial processing.

The processes are advantageously to remove contaminants and degradation products from amines used by refinery, natural gas and petrochemical processes to remove certain contaminants, including acid gases. Other technologies require further processing of the waste stream, higher loss of solvent, or both. When amine is processed a tar like bottoms phase is obtained, and when physical solvents like Selexol™ are processed the resulting contaminant is in liquid bottom phases. While conditions can of course be selected to obtain wet bottom phases, for example wet salts when processing glycol, in a preferred embodiment waste composition of salt or other contaminants will have from 20 wt % or less solvent on a dry basis or will be substantially dry.

Another embodiment includes a process of treating a contaminated amine stream, or alternatively treating a contaminated Sulfinol™ solvent, which is a blend of a tertiary amine, an alkanolamine or ethyl-alkanolamine, and Sulfolane™ (tetramethylene sulfone, tetrahydrothiophene-1,1-dioxide), by mechanically forming a moving thin film on a heated substrate under conditions of temperature and sub-atmospheric pressure, wherein the residence time on the thin film evaporator is sufficient to remove substantially all the amine stream or hybrid amine stream, respectively, and the recovered material are recovered in dry powder form, or organic contaminants are recovered in substantially solvent-free form. Heavy hydrocarbon contaminants are also readily removed from the contaminated amine/hybrid amine stream. The thin film may be mechanically maintained by continuous wipers to a thickness of between 1 mm and 5 mm. This obtaining of the contaminant salts, and the like, as powder or as a dry material, greatly simplifies waste handling.

Another aspect is an embodiment which includes a process of treating a contaminated Selexol™ solvent, which is a blend of compounds, by mechanically forming a moving thin film on a heated substrate under conditions of temperature and sub-atmospheric pressure, wherein the residence time on the thin film evaporator is sufficient to remove substantially all the amine stream or hybrid amine stream, respectively, and the recovered contaminant material is optionally stored at reduced pressure. Heavy hydrocarbon contaminants are also readily removed from the contaminated Selexol™. The improvement over prior processes is in the recovery from the thin film of solvent-free contaminant material. The thin film is mechanically maintained by continuous wipers to a thickness of between 1 and 5 mm thickness. The consistency of the recovered contaminants is variable.

The chemical-type gas treating solvents which can be advantageously treated with the described process include alkylated propylene glycols and/or alkylated ethylene glycols, ethylene/propylene glycols (for example dimethyl ethers of polypropylene glycol, propylene glycols and/or ethylene glycols, Selexol™, Sulfolane™, Sulfinol™ D, Sulfinol™ M, generic amines, and especially alkanolamines including for example monoethanolamine, diethanolamine, triethanolamine, 2-(2-Aminoethoxy)ethanol covered under CAS 929-06-6, methyl diethanolamine, di-isopropanolamine, Flexsorb™ proprietary alkanolamine, and Cansolv™ proprietary alkanolamine, as well as propylene carbonate, and N-methyl pyrrilidone. The processes are advantageously used to remove contaminants and degradation products from solvents, such as amines and glycols, used by refinery, natural gas and petrochemical processes to remove the majority constituents of interest. These solvents are used in gas processing and in refineries to remove sour gas and acid gases, and hydrate inhibition (remove water).

By "glycols" we mean alkyl glycols, alkylene glycols, poly-(alkylene)glycols, and alkyl ethers of the foregoing, and other glycols mentioned specifically herein.

It is also envisioned to utilize a pre-separation technology, especially with glycols but also with amines, which can remove a portion of contaminants, typically removing volatile contaminants, water, and some solvent, before introducing the feed stream into the TDSX™ thin film mechanically agitated evaporator. In particular for glycol, pretreating with a forced circulation evaporator to evaporate the water from glycol before the thin film evaporator needed to utilize this process is anticipated for many commercial applications.

Another embodiment includes a process of treating to remove certain contaminants from a contaminated physical solvent, a contaminated chemical solvent, or a contaminated hybrid chemical/physical solvents, for example a contaminated glycol stream, or a contaminated amine stream, by mechanically forming a moving thin film of the contaminated solvent on a heated horizontally-orientated evaporator substrate under conditions of elevated temperature and subatmospheric pressure, wherein the residence time on the thin film evaporator is sufficient to remove substantially all the solvent, for example the glycol or amine stream, respectively, and the ionic contaminant material or organic contaminants are recovered in dry powder form and/or organic contaminants are recovered in substantially solvent-free form for example as a tar or liquid. The thin film is mechanically maintained by continuous wipers to a thickness of between 1 mm and 5 mm.

Another embodiment includes a method of treating a contaminated glycol stream, the process comprising: 1) providing a first stream of contaminated glycol comprising glycol, water, and dissolved salts; 2) mechanically forming and maintaining a moving thin film on a horizontally-orientated heated substrate under conditions of elevated temperature and sub-atmospheric pressure, at a pressure of 1 to 10, typically 3 to 5 kPa, and at a temperature of greater than 100 degrees C., for example between 160 to 190, typically 170 to 180 degrees C. (where the temperature range will differ for different solvents), wherein the thin film is wiped to maintain film thickness between about 1 to about 5 mm: 3) condensing and recovering the glycol and water stream, and 4) recovering the salts from the thin film evaporator as substantially dry powder. By substantially dry we mean the solids comprise greater than about 50% by weight solids, preferably greater than about 80% by weight solids, the remainder being glycol, water, and other contaminants.

Advantageously and importantly, the thin film evaporator apparatus contains rotors or wipers to continuously form and maintain the thin film on a horizontally-orientated substrate. The economic attainment of solvent-free contaminant material from a steady state thin film is not possible unless the thin film is mechanically maintained. A preferred horizontally orientated substrate is a cylinder, where the axis of the cylinder is horizontally orientated, and it is recognized that a substantial portion of the evaporating substrate, be it the interior wall of the cylinder or the exterior wall of the cylinder, may not be horizontally orientated. A commercial embodiment of a preferred thin film evaporator is the Artisan® Rototherm E Thin™ Wiped Film Evaporator. The use of the mechanically maintained thin film evaporator, in conjunction with pressures and temperatures known to those of skill in the art, allows for up to 99% evaporation in a single pass. An exemplary apparatus can be found at www.artisanind.com/ps/equipment/rototherm features.html which shows a cross section of a commercially available horizontally orientated cylinder type thin film evaporator apparatus. In the embodiment shown, the wiper is depicted as maintaining a "bow wave" of material, where this bow wave deposits additional material to replace material lost to vaporization, and thus to maintain consistent thickness. The wipers have a body, and in the context of wipers moving in a cylinder, the wiping edge of the wipers can be called a rotor blade. While the figure shows text indicating that the wipers move at 30 to 60 feet per second, any appropriate velocity can be used. The Artisan Industries' Rototherm™ is a specialized evaporator which uses a high-speed rotor that creates centrifugal force, which keeps the feed against a heated horizontal cylinder wall. A turbulent thin film between the rotor blades and wall covers the entire heated surface. The turbulent thin or wiped film creates high heat transfer efficiency, minimizing the area required for evaporation. The film is continuously renewed by the incoming feed as the progressively more concentrated material moves towards the bottoms discharge nozzle. Product residence time in the Rototherm™ is generally measured in seconds, minimizing degradation of heat-sensitive materials.

The use of a wiper to maintain the film thickness is highly beneficial, as the viscosity and other properties of the liquid change considerably as the glycol, or amine, is quantitatively removed. Further, fouling is substantially reduced.

Preferred operation for glycol is at a pressure of 1 to 10, typically 2 to 5 kPa, at a temperature of 160 to 190, typically 170 to 180, degrees C. This process is optimally operated at approximately 2 kPa absolute pressure in order to obtain a discharge of dry flowable solids.

Typical thin film evaporators are the known vertical wall, where the thin film is maintained by flow due to gravity. Such a process is not useful for this invention, as this type of thin film cannot tolerate high solids loading as will be experienced as the amount of glycol or amine removed approaches 99%. Further, the use of the mechanically maintained thin film provides agitation and turbulence, thereby increasing efficiency. Surprisingly low temperatures are needed, so contaminants formed at higher temperature distillation will not form in the process of this invention. Other advantages of this mechanically formed and maintained film include ability to handle changing and very high viscosity (up to 2 million centipoise); negligible pressure drop; High turndown ratio (10:1 or better); High surface to volume ratio, a fully wetted wall at all evaporation and flow rates where the thin film is unaffected by gravity; and no dry spots and minimal to no fouling. Generally a wiper maintains a "bow wave" of material, where this bow wave deposits additional material to replace material lost to vaporization, and thus to maintain consistent thickness, and constantly renews the material at the heat transfer surface. The wipers have a body, and in the context of wipers moving in a cylinder, the wiping edge of the wipers can be called a rotor blade.

Particularly useful applications for this technology include: Amine Solutions—removal of heat stable salts and other degradation products where minimization of wastes or rinse water is required, or removal of degradation products which cannot be removed by ion exchange technology, e.g., THEED (tris-hydroxyethylethylenediamine); Glycol Solutions—removal of salts and corrosion products from natural gas processing plant's dehydration systems; Sulfolane™ Extraction Solvent—removal of contaminants and degradation products from systems which extract cyclic from noncyclic organics in refinery recovery streams; and Selexol™—removal of contaminants and degradation products.

EXAMPLES

A horizontal, mechanically aided thin-film Rototherm™ evaporator was used for these examples unless otherwise specified.

Contaminated glycols when fed into the thermal horizontally orientated wiped film evaporator returned clean glycol condensed from the tops and substantially dry flowable salts and other solids from the bottoms. Slurries of salts can also be obtained, including slurries of salts and liquid contaminants or slurries of salts in solvent.

The following discussion relates to treatment of amines, but is also applicable for treatment of glycols. In one embodiment tested with an amine stream, stripping steam was introduced through a critical flow nozzle on selected runs in order to completely sweep the bottoms material of valuable amines thereby increasing recovery. Once the liquid feed entered the Rototherm shell, the water and amines were removed from the feed by turbulent liquid thin-film evaporation as the feed flowed along the inner sidewalls of the Rototherm™ jacketed process section. The concentrated bottoms stream exited the mechanical thin film evaporator by gravity into a 1-gal glass jar. The water and amines evaporated from the feed exited the Rototherm™ through the 4" vapor outlet, traveling through a vapor body and then to a condenser where the water and amines were condensed and labeled as Distillate. The vent stream from the condenser then entered a cold trap cooled with dry ice, immediately upstream of the vacuum pump, which was installed to catch any remaining condensable exiting the condenser. All output streams (bottoms, Dl distillate, and cold trap distillate) were collected in glass jars that were periodically isolated from the process and changed out as needed.

| Pilot Plant Degraded Amine Feed Characterization | | | | |
|---|---|---|---|---|
| Feed Sample | Water, wt. % | DEA, wt. % | THEED, wt. % | HSS, wt. % |
| 1000 | 65 | 27 | 5 | 3 |
| 2000 | 67 | 28 | 5 | 0 |
| 3000 | 69 | 28 | 2 | 1 |

A pilot plant test was performed on various amine streams. Note: All samples were pretreated to remove hydrogen sulfide and enough caustic added to free the amines for recovery. The first feed contained approximately 5% THEED, 65% water, 27% amines and the balance salts as described above. This feed was not pre-treated to remove any of the salts. The second feed was similar in composition to the first but the feed was pre-treated to remove some of the salts. The third feed contained approximately 2% THEED, 70% water, 28% amines and the balance salts. This feed was not pre-treated to remove any of the salts.

Typically amine is run with the thin film maintained at between 148.88 degrees C. and 232.22 degrees C., and at a pressure (absolute) of between 0.133 and 13.33 kPa, advantageously between 0.67 and 3.33 kPa. The steam-sparged mechanically maintained thin film evaporator successfully recovered DEA from all of the feed materials that were processed with liquid recoveries ranged to 99.8% when operating at conditions near the optimal, vacuum of 1.33 kPa and film temperatures from 174.44 degrees C. to 212.78 degrees C. These temperatures vary depending on concentrations of THEED and heat stable salts in the degraded amine feed.

Based on the observations and results of the amine tests, the process effectively removed inorganic salts, non-volatile heat stable salts, and up to 60% of the liquid THEED entering with the degraded DEA feed in a single evaporation step. The other liquid degradation product is known as bis-HEP. It was only recovered at 15% of that incoming with the feed. The pilot plant test processed three different contaminated amine feedstocks, and effectively recovered up to 99.8% of the diethanolamine (DEA) in the feed, while discharging a concentrated bottoms stream consisting of heat stable salts, Tris(hydroxyethypethyelendiamine (THEED), Bis(hydroxyethyl)piperazine (bis-HEP), and trace residual DEA and uncharacterized organic material. The degraded DEA solutions treated in the mechanically maintained thin film evaporation process recovered 98+% of the incoming DEA and water while removing 60% of the undesirable THEED and 15% of the bis-HEP plus all heat stable and inorganic salts from the feed solution in a single step. The pilot process ran steadily during the amine pilot trial and there were no signs of fouling or accumulation of solids or concentrated material on the jacketed walls of the evaporator. A steam sparge through the thin film evaporator is required to maximize DEA recovery. Without steam sparge the DEA recovery was limited to approximately 87%, but a feed to sparge rate ratio of 14-21 weight per weight yielded greater than 95% DEA recoveries. While sparge gas can be any inert gas, steam is preferred to simplify condensation of the vapors.

The concentration of THEED in the feed material affects the optimum operating temperature required to maximize DEA recovery. For the feed containing 5% THEED, an optimum film temperature of approximately 210 degrees C. was required to achieve greater than 95% recovery. With a feed containing 2% THEED, the film temperature of approximately 173.89 degrees C. was sufficient, at an operating pressure of 1.33 kPa.

The material balances performed on the pilot plant runs identify significant and previously unidentified degradation products in the degraded amine solutions, Depending on the processing conditions and the source for feed, the removal of those constituents ranged from 40% to 84%.

A pilot plant test was performed on a contaminated glycol stream. Sample identifiers and characteristics are shown below.

| Pilot Plant Salt Degraded Glycol Feed Characterization | | | |
|---|---|---|---|
| Feed Sample | Water, wt. % | MEG, wt. % | Salts, wt. % |
| 4000 | 81.7 | 15 | 3.3 |
| 5000 | 9.6 | 88 | 2.4 |
| 6000 | 0 | 90 | 10 |

Based on the observations and results of both tests, the pilot plant effectively removed inorganic salts from the glycol water solutions. The salts were discharged as a free-flowing dry powder while all the glycol and water was recovered as a salt-free solution ready for reintroduction into the natural gas process. The dilute MEG solution in feed sample 4000 typifies a very weak glycol solution without benefit of pre-evaporation of the incoming water prior to being fed to the thin film evaporator. This is an example of MEG highly diluted with produced water and salt. The concentrated MEG solution in feed sample 5000 represents one of a dilute solution subjected to pre-evaporation of the majority of the water before being fed to the thin film evaporator. This would be typical of a MEG mixture withdrawn from MEG regenerator reboiler. The concentrated MEG solution in feed sample 6000 represents one of a preevaporated regenerator reboiler solution with the water removed and including salts precipitated during the evaporation step before being fed to the thin film evaporator as slurry. This would be typical of concentrated mixture withdrawn from MEG regenerator reboiler.

Another Example was run on contaminated Sulfolane™. Sulfolane™ is difficult to clean with ion exchange. Contaminated Sulfolane™ was obtained from a petrochemical plant. In order to model the wipe film evaporator, 175 mL of the contaminated Sulfolane™ sample was mixed with 35 mL of distilled water and placed in a distillation flask. The sample was stirred, heated and a vacuum applied. A first fraction was distilled at 58 degrees C. and 15.99 kPa; it is believed that this fraction was mostly water. A second fraction was distilled at 185 degrees C. and a pressure of 7.33 kPa. The contaminated sample was black and dirty in appearance. The distilled sample was nearly water white and free from particles. The bottom fraction from the distillation was a black tar that solidified at room temperature.

Another Example was run with contaminated Selexol™. A dark, contaminated sample of Selexol™ was obtained from a commercial solvent reclamation company. Initial analysis suggested the sample contained about 69% (all % by weight) Selexol™, about 6% water, and about 26% unidentified organic contaminants. The contaminated material was passed through a horizontal wiped film evaporator under conditions to remove water, that is, at about 212.78 degrees C. and 13.33 kPa absolute pressure. The material separated from the contaminated stream contained 60% water and 40% Selexol™. The "bottoms" contained about 70.6% Selexol, about 30% unidentified organic contaminants, and no water. This bottoms sample was then run a second time through a horizontally orientated mechanically wiped film evaporator, under conditions to remove organic contaminants, that is, 223.89 degrees C. and 1.33 kPa absolute pressure. In this second run, Selexol™ is recovered and condensed, and the bottoms are contaminants. When run at 257.78 degrees C. and 0.67 kPa absolute pressure, the recovered solvent was substantially clear and contained about 81% Selexol™ and 19% unidentified hydrocarbons, and the bottoms contained about 30% Selexol™ and 70% organics. When the same sample was run at 223.89 degrees C. and 1.33 kPa absolute pressure, the recovered solvent was clear and contained about 98% Selexol™ and 2% unidentified hydrocarbons, and the bottoms contained about 50% Selexol™ and 50% organics.

The THP (total petroleum hydrocarbons) concentrations were monitored. THP values in the initial feed were 129 ppm (parts by million by weight), and a substantial portion of this (102 ppm) could be found in the first tops to remove water, leaving about 90 ppm in the bottoms. During subsequent runs to remove organics, the THP differentiated with the contaminant-containing bottoms having about twice the THP concentration as the recovered Selexol™ from the tops, e.g., 60 to 70 ppm in the tops compared to 120 to 140 ppm in the bottoms. Acetate, at an initial concentration of 18 ppm in the contaminated Selexol™ feed, was totally removed in the dewatering stage, and the acetate stayed with the aqueous phase. Sodium and calcium present in the original contaminated Selexol™ feed were reduced, though at the very low concentrations present it is difficult to quantify, with sodium, iron, and calcium each being reduced by half or more, based on the concentration in the incoming feed compared to the concentration of the recovered cleaned Selexol™.

There were a number of pilot plant tests performed. At film temperature of 148.89 degrees C., the system separated and recovered only a small fraction of the Selexol™ present. At pressures above 1.60 kPa, the system operated at low efficiency. At pressures of 0.67 kPa and temperatures of 223.33 to 257.78 degrees C., the Selexol™ recovery increased to between 65 and 82% recovery. At 0.27 kPa and temperatures of 223.33 to 257.78 degrees C. Selexol™ recovery increased to between 90% to 99% of the Selexol™ in the original feed.

It is clear that the process can be tailored to meet client specifications on recovered product. The remaining bottoms can be run again to further separate the Selexol™ from the unidentified hydrocarbons. It is shown that sometimes two passes through the horizontally orientated wiped film evaporator may be required, the first to remove light components and the second to remove (and re-condense and collect) the solvent from heavier contaminant components.

The contaminants recovered, and the physical state of the recovered contaminants, depends on the nature of the solvent and the contaminants. For glycol streams, water can be removed if desired in a first pass, and dry salts are recovered in the bottoms of the final pass through the horizontally orientated wiped film evaporator. With amines, the recovered bottoms are tarry with little solvent. With Selexol, the recovered solvent stream from the tops contains about 80 to 98% by weight Selexol and from about 20% to 2% unidentified organics, and the bottoms contain more than 50% unidentified organics.

Monoethylene glycol (MEG) Reclamation consists of removal of the salts, corrosion compounds, and other heavy compounds that end up in the MEG after MEG Regeneration. The salts build up unless removed, and when they build up to critical levels while containing acids, they become very corrosive. The combination of salts, corrosion products, and asphaltines create tremendous fouling problems for the reboiler on the regenerator. Pilot plant tests demonstrated excellent continuous dry salt discharge from a Rototherm™ pilot unit under all feed conditions, a) dilute salt and glycol, b) 80% MEG and water saturated with salt, and 88% MEG with 12% crystallized salt. The obtaining of free-flowing dry salts from the thin film evaporator treating a glycol stream was an unexpected result.

More than one evaporation technology may be applied to reclaim amines with very low vapor pressures. For example, Forced Circulation Evaporation is a known process to clean solvents, where this may be used in conjunction with the thin film process described here.

We can obtain ultra-high recovery with the wiped film evaporator. To reclaim amine for streams containing heat stable salts, the operator may choose the horizontal wiped film evaporator process, recovering both water and amines. To reclaim from a stream devoid of HSS, the operator may reclaim amine using the horizontal wiped thin film evaporator process described here.

Regardless of feed streams treated, the wiped film evaporator requires utilities and waste disposal support in order to effectively operate. These are: 1) evaporative heating supplied to the evaporating substrate of the evaporator; 2) cooling and/or chilled water supplied to condense the evaporated recovered components; 3) a vacuum system sufficient in size to maintain at least a 1.33 kPa vacuum on the system including process non-condensables; and 4) an effective removal system for extracting powders, solids, tars and liquids from the evaporator while maintaining operating vacuum.

An 85 sq ft TDSX™ horizontally orientated mechanically maintained thin film evaporator runs mixtures of water and various amines at different rates. Heat transfer flux BTU/sq ft/hr varies with the organic content in a water mixture. The same is true for mixtures of water and glycols.

The thin film is mechanically maintained by wipers. Advantageously wipers move at a velocity of between 1 and 100 feet per second, with wipers passing over a surface at least once every five seconds or so, preferably between 1 and 10 times per second. Wipers move perpendicular to the product flow, so as to not push untreated product out the exit. If the evaporator surface is the inside surface of a tube, rapid spinning of wipers in the tube provides centripetal force to force the stream against the evaporator wall. Heat is supplied through the wall.

The invention is meant to be illustrated by, and not limited to, the examples.

What is claimed:

1. A steady-state method of treating a contaminated solvent stream with a horizontal thin film evaporator having a heated substrate surface, the process comprising:
   a. providing to the horizontal thin film evaporator a feed stream of contaminated solvent comprising
      i. an amine, a glycol, or mixture thereof, wherein the amine comprises one or more alkanolamines and
      ii. one or more contaminants comprising salts, organics, solids, or mixtures thereof;
   b. forming and mechanically maintaining a thin film of contaminated solvent disposed on the heated substrate surface at sub-atmospheric pressure, said thin film having a thickness, wherein the thin film is repeatedly wiped to maintain the film thickness and to move the thin film along the heated substrate surface;
   c. recovering a tops vapor phase comprising the solvent, forming a recovered solvent, wherein the concentration of contaminants in the recovered solvent is substantially reduced from the concentration of contaminants in the feed stream, and
   d. recovering a bottoms phase from the heated substrate surface, wherein said bottoms phase comprises less than 20% by weight solvent.

2. The method of claim 1, wherein the bottoms phase recovered from the heated substrate surface comprises less than 10% by weight solvent.

3. The method of claim 1, wherein the bottoms phase recovered from the heated substrate surface comprises less than 5% by weight solvent.

4. The method of claim 1, wherein the feed stream of contaminated solvent comprises a glycol solvent and contaminant salts, and wherein the bottoms phase recovered from the substrate surface is a flowable powder.

5. The method of claim 4, wherein the feed stream is a contaminated glycol stream comprising contaminant salts, and wherein the bottoms phase recovered from the heated substrate surface is a flowable powder containing substantially no glycol.

6. The method of claim 4, wherein the tops vapor phase comprising the solvent is condensed to recover the glycol, wherein the glycol recovered is 95% by weight or more of the glycol in the feed stream, and wherein the bottoms phase comprises 10% by weight or less of solvent.

7. The method of claim 4 wherein the tops vapor phase comprising the solvent is condensed to recover the glycol, wherein the glycol recovered is 99% by weight or more of the glycol in the feed stream based upon solvent mass balance, and wherein the bottoms phase comprises 5% by weight or less of solvent.

8. The method of claim 4 wherein the glycol is selected from ethylene glycol, propylene glycol, diethylene glycol, triethylene glycol, tetraethylene glycol, polyethylene glycol, polypropylene glycol, polyethylene/propylene glycols, or mixtures thereof.

9. The method of claim 1, wherein the feed stream of contaminated solvent comprises an amine solvent and contaminants comprising organics and thermally stable salts, wherein the bottoms phase recovered from the heated substrate surface is a tar-like material which contains 20% by weight or less of the amine solvent.

10. The method of claim 9, where the amine solvent comprises alkanolamines selected from the group consisting of monoethanolamine, diethanolamine, triethanolamine, 2-(2-Aminoethoxy)ethanol, methyl diethanolamine, di-isopropanolamine, and mixtures thereof.

11. The method of claim 9, wherein the tar-like material recovered from the heated substrate surface comprises 10% by weight or less of the solvent.

12. The method of claim 9, wherein the tar-like material recovered from the heated substrate surface comprises 5% by weight or less of the solvent.

13. The method of claim 9, wherein the tar-like material recovered from the heated substrate surface comprises 5% by weight or less of the alkanolamine.

14. The method of claim 9, wherein the tops vapor phase comprising the solvent is condensed to recover the solvent, wherein the alkanolamine recovered is 95% by weight or more of the alkanolamine in the feed stream, and wherein the bottoms phase comprises 10% by weight or less of alkanolamine.

15. The method of claim 9, wherein the tops vapor phase comprising the solvent is condensed to recover the alkanolamine, wherein the alkanolamine recovered is 99% by weight or more of the alkanolamine in the feed stream, and wherein the bottoms phase comprises 5% by weight or less of alkanolamine.

16. The method of claim 1, wherein the heated substrate surface is a substantially horizontal plane or is a cylinder wherein the axis of the cylinder is substantially horizontal, and wherein the thin film is mechanically to maintain the film thickness and move the thin film along the heated substrate surface.

17. The method of claim 1 wherein the sub-atmospheric pressure is 10 kPa or less.

18. The method of claim 1 wherein the sub-atmospheric pressure is 5 kPa or less.

19. The method of claim 1 wherein the sub-atmospheric pressure is between 1 and 20 kPa.

20. The method of claim 1, further comprising a step of introducing a sparge gas above the thin film of step b to facilitate removal of the tops vapor phase from the horizontal thin film evaporator.

21. The method of claim 20, wherein the solvent comprises one or more alkanolamines.

22. The method of claim 1, wherein the method comprises:
   a. providing contaminated solvent to a mechanically-formed moving thin film on a horizontally orientated heated substrate surface under conditions of elevated temperature and sub-atmospheric pressure of between 1-20 kPa, wherein the contaminated solvent forms a mechanically maintained thin film on the horizontally orientated heated substrate surface; and b. mechanically moving and agitating the thin film for a time sufficient to remove substantially all the solvent contained in the thin film, wherein the tops vapor phase moves in a direction substantially perpendicular to the thin film's movement.

\* \* \* \* \*

UNITED STATES PATENT AND TRADEMARK OFFICE
CERTIFICATE OF CORRECTION

PATENT NO. : 10,010,809 B2
APPLICATION NO. : 14/768947
DATED : July 3, 2018
INVENTOR(S) : Hagerman et al.

Page 1 of 1

It is certified that error appears in the above-identified patent and that said Letters Patent is hereby corrected as shown below:

In the Claims

In Claim 1 at Column 15, Line 34, the text "a thickness," should be changed to -- a film thickness, --
In Claim 4 at Column 15, Line 54, the text "the substrate surface" should be changed to -- the heated substrate surface --
In Claim 22 at Column 17, Lines 4-5, the text "direction substantially perpendicular to the thin film's movement" should be changed to -- countercurrent flow with respect to the thin film direction of movement --

Signed and Sealed this
Second Day of October, 2018

Andrei Iancu
*Director of the United States Patent and Trademark Office*